(12) United States Patent
Siebler et al.

(10) Patent No.: US 6,343,229 B1
(45) Date of Patent: Jan. 29, 2002

(54) DEVICE FOR MEASUREMENT AND ANALYSIS OF BRAIN ACTIVITY OF BOTH CEREBRAL HEMISPHERES IN A PATIENT

(76) Inventors: Mario Siebler, Girardstatr. 40, D-42109, Wappertal; Stephen Theiss, Friedenstrabe 39, D-40219, Dusseldorf, both of (DE)

(*) Notice: Subject to any disclaimer, the term of this patent is extended or adjusted under 35 U.S.C. 154(b) by 0 days.

(21) Appl. No.: 09/464,274

(22) Filed: Dec. 15, 1999

Related U.S. Application Data

(63) Continuation of application No. PCT/EP98/03585, filed on Jun. 15, 1998.

(30) Foreign Application Priority Data

Jun. 15, 1997 (DE) .......................................... 197 25 214

(51) Int. Cl.[7] .................................................. A61B 5/05
(52) U.S. Cl. ........................................ 600/544; 600/545
(58) Field of Search ................................ 600/544, 545

(56) References Cited

U.S. PATENT DOCUMENTS

| 4,339,810 A | 7/1982 | Nichols et al. |
| 4,412,457 A | 11/1983 | Callahan et al. |
| 5,230,346 A | 7/1993 | Leuchter et al. |
| 5,269,315 A | 12/1993 | Leuchter et al. |
| 5,357,976 A | 10/1994 | Genquan Feng |
| 5,392,788 A | 2/1995 | Hudspeth |
| 5,458,117 A | 10/1995 | Chamoun et al. |

FOREIGN PATENT DOCUMENTS

| DE | 1 961 593 | 9/1969 |

*Primary Examiner*—Mark Bockelman
(74) *Attorney, Agent, or Firm*—Woodbridge & Associates, P.C.; Richard C. Woodbridge

(57) ABSTRACT

The invention relates to a method and device for measuring cerebral electrical activity in a patient. Cerebral electrical activity is measured in the form of electrical signals. Said signals are amplified and converted to signals which are then stored. The digitized signals and/or the stored digitized signals are processed as individual signals and as two channel signals for both cerebral hemispheres of the patient. A brain function index is thus determined to measure the normality of the patient's brain function.

9 Claims, 1 Drawing Sheet ary perturbations, frequently manifest themselves in alterations
DEVICE FOR MEASUREMENT AND ANALYSIS OF BRAIN ACTIVITY OF BOTH CEREBRAL HEMISPHERES IN A PATIENT This application is a continuation of PCT/EP 98/03585 filed Jun. 15, 1998.

BACKGROUND OF THE INVENTION

1. Field of the Invention

The invention concerns a process and a device for measuring the electrical brain activity and, in particular, evaluation of the measurement results.

2. Description of the Related Art

In medicine, one is confronted by the problem of measuring the acute phase functional capacity of the human brain after the occurrence of, for example, a stroke.

In 1910, Berger discovered that the electrical activity of the brain could be measured as an electroencephalogram (EEG) by using sensitive amplifiers on the human scalp. Brain damage such as, for example, circulatory perturbations, frequently manifest themselves in alterations in the EEG; that is, changes in the signal frequencies or amplitudes. There is locus specificity; that is, resolution of the exact location of the damage site in the brain in contrast with imaging procedures such as, for example, computer tomography of the cranium, is very restricted. On the other hand, the temporal resolution of brain activity or alterations in activity is substantially better. In addition, the full extent of the brain insult can be seen only after passage of hours or days in tomography, by which time the tissue is irreparably damaged.

Measurement of an EEG is, for example, presented in the U.S. Pat. Nos. 5,392,788 and 5,269,315 documents.

The system described in U.S. Pat. No. 5,392,788 is used to test the patient's reaction to stimuli. In this instance, the data are processed after acquisition so that they can be compared to baseline values. Deviations between data and baseline values are used to determine irregularities.

U.S. Pat. No. 5,269,315 describes a process and a device for the interpretation of brain currents, whereby certain brain activities are combined in a primary frequency range and in a second frequency range. After application of a Fourier transformation to the digitally measured data the data is further processed by segregating the entire output range obtained by the Fourier transformation into an absolute output and a relative output.

U.S. Pat. No. 5,458,117 describes a system and a process for derivation of a diagnostic index from 19 measured EEG signals. At evaluation of the signals, for example, a fast Fourier transformation or a cross-correlation is applied to all signals measured. The determination of the diagnostic index is relatively costly due to the many signals that must be measured.

Consequently, to date neither purely clinical methods nor imaging processes, such as nuclear spin tomography, are adequate for objective determination of the extent of brain damage in the acute phase, since there is no simple answer to the question, whether the symptoms presenting in the patient are caused by a circulatory perturbation at all. A much higher outlay for equipment is required in imaging procedures and in the acute phase; that is, in the few hours following the appearance of the symptoms, they do not allow a detailed determination to be made of the extent of the damage. However, since it is particularly important in the acute phase that the correct therapeutic decisions are made, there is considerable interest in rapid and uncomplicated diagnostic methods.

DE-OS 19 61 593 describes the performance of a comparison of EEG activity of the hemispheres. In this instance, the selection of electrode placement is similar to that in the present invention. A correlative coefficient indicates in a specific time whether the two channels being examined exhibit the same polarity. If, in addition, the amplitudes of the signals of the analysis are added, as is indicated (see 5.17) in DE-OS 19 61 593 using the Pearson's Product-Moment-Correlation Coefficient, the value of the correlation function of the two channels is determined at a fixed time lag [lit. "shift"] At (here up to 100 bit at 1 kHz=0.1 sec). The correlation coefficient indicates the instantaneous polarity behavior; no temporal track is calculated or temporal averaging done. Moreover, in the procedure described in DE-OS 19 61 593 so-called "evoked potentials" are measured with priority; this means that the patient is subjected to a stimulus (most often visual), whereupon the electrical cortical response is measured.

U.S. Pat. No. 4,412,547 describes an apparatus for monitoring brain activity, whereby the measurement process is accomplished with few EEG electrodes. In the subsequent analysis of the signals measured, however, only very rough characteristics of the EEG signal are compared: the outputs of the individual channels (if required, after frequency filtering) and the "average frequency" determined using a disputable process ("zero crossing") for such a complex signal. In the process described in U.S. Pat. No. 4,412,547 a complex mix of frequencies is converted into a single frequency display or indication.

Starting with the device described in U.S. Pat. No. 269, 315, the invention takes up the problem of creating a device, by means of which the physician can rapidly obtain a decision-criterion at examination of a patient apparently affected by stroke, that will allow the most certain prognosis of the extent of the brain damage and its future development.

SUMMARY OF THE INVENTION

Pursuant to this invention, very detailed properties of the measured electrical signals are used. Thus a sample analysis done on the FFT of the individual channels and the FFT of the correlation function relevant to its peak structure (location, height and breadth). The structural properties that are then calculated are compared in order to ultimately determine a derived magnitude, namely the brain function index, that provides for a simpler interpretation. In particular, pursuant to the invention, an analysis of the frequency structure of the entire correlation function is done.

With the process described in the invention for measuring electrical brain signals, particularly in humans, a quick and effective analysis of the measured signals can be performed and they can be digitized, stored and subsequently analyzed on a computer.

The device described in the invention makes possible stepwise processing of the brain waves measured on the patient, whereby it is particularly advantageous, that the procedure can be performed in conjunction with other clinical diagnostic procedures.

The invention provides a simple, clear interpretation of the results as well as easy operation, for example, by nursing staff. In addition, the level of error security is very favorable.

In the following, the invention is described in detail using realization examples with reference to the illustration.

DETAILED DESCRIPTION OF THE PREFERRED EMBODIMENT

Figure 1:
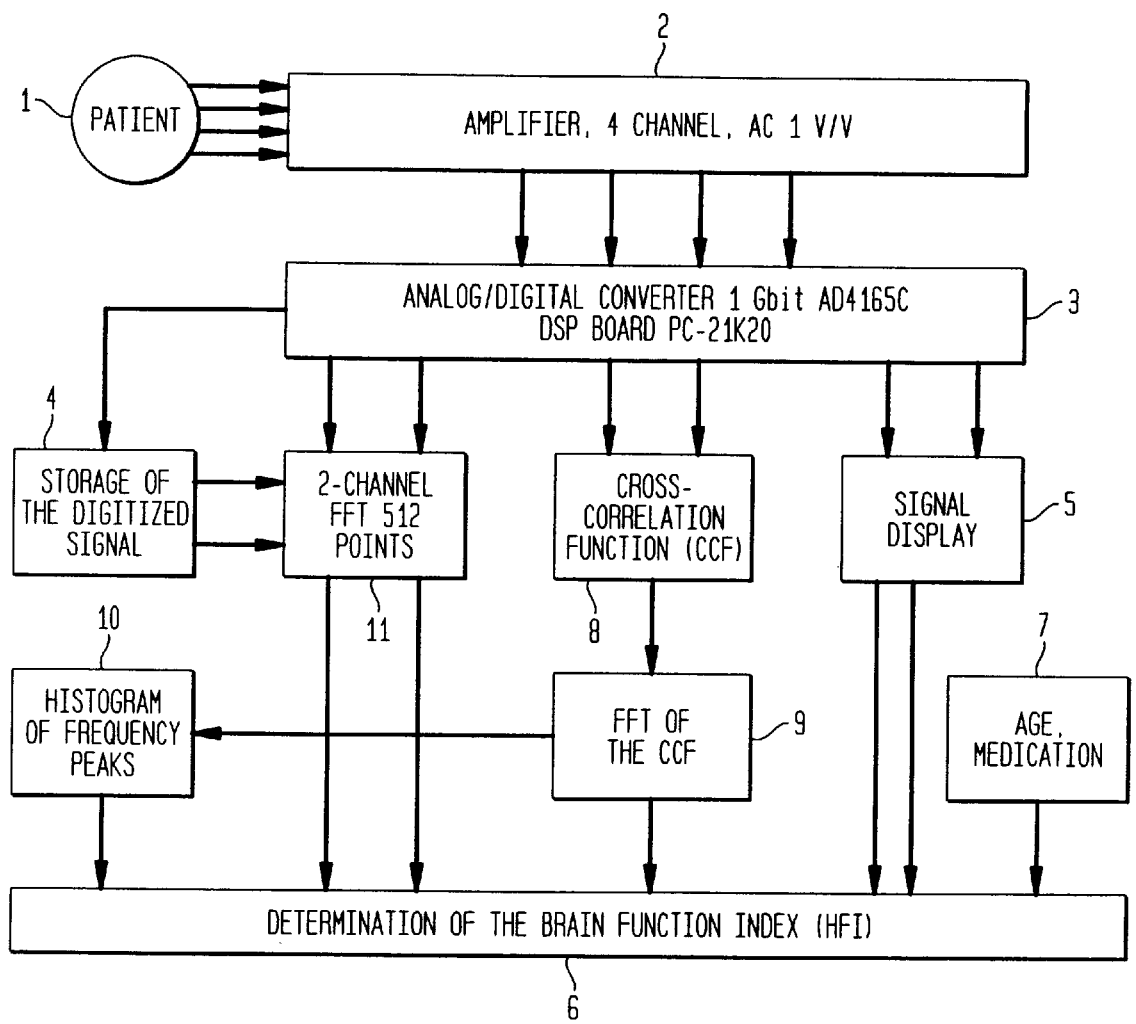
FIG. 1 illustrates the elements of the invention in a block diagram form according to the preferred embodiment thereof.

Signal acquisition (1) is done on the patient's head. Measurement electrodes are placed at five points on the patient's head: one pair of measurement electrodes on each side of the head and another electrode on the forehead for grounding. The electrical brain signals (EEG) are derived from the measured signals and fed into the input of a DC/AC amplifier. The leads must be well shielded because the EEG voltages are in the $\mu V$ range. The best shielding is provided by so-called "active shielding."

The amplifier used in the realization example of the invention has a sensitivity of from 1 to 5000 JLV/V, which corresponds to an amplification of from 200 to 1,000,000. It is connected via a serial interface of a notebook PC and configurable with respect to channel selection, the measurement range settings, switching of high and low pass filters with differing limit frequencies, and impedance measurement and can be expanded to up to eight channels. For suppression of undesired frequencies in the signal a low pass filter with an upper limit frequency of 30 Hz is connected in the amplifier and for clipping the d.c. voltages, a high-pass filter with a lower limit frequency of 0.2 Hz is wired in. Automatic regular impedance measurement is done using a current (1)=5 V/4.7 M$\Omega$=1.06 $\mu A$ at a measurement frequency of 100 Hz (in the present example, once in 5 minutes) and secures, for example, using an acoustical warning signal, the measurement against unnoticed loosening of the electrodes, which could happen if the patient moves. Automatic adaptation of the amplifier measurement range prevents "clipping" on possible overloading of the amplifier. The assurance of satisfactory signal quality at acquisition is critical in safeguarding agains erroneous measurements; placement of the electrodes on the head, the impedance of the transfer from the electrode to the head and the adjustment of the measurement range of the amplifier are all important in this respect. The continuous display of signals is an additional safeguard against erroneous measurements. The test measurements are done at contact resistances of approximately 1–12 k$\Omega$. The amplification factor was about 200,000.

Signal processing is done next. Said complete processing of the signals occurring at the output of the amplifier (2) and which lie in the range of 1 V, is done in a PC or a notebook computer (3) with a docking station. Two special PC expansion cards are used. One of the cards is a measurement value pick-up card (in the present example an MWE board with the type designation AD416SC manufactured by STAC GmbH) and the other one is a digital signal processor card (in the present example a DSP board with the type designation PC-21K20 manufactured by STAC GmbH) for numeric processing of the collected and digitized signals.

The measurement value acquisition card has four differential inputs that are set up for voltages up to ±10 V, can be freely selected DC or AC coupled and each one contains its own "sample-and-hold" [measuring] amplifier as well as one each 16-bit-A/D converter with a 90 dB volume dynamic. Special emphasis is placed on optimally adapted anti-aliasing filters. The scanning of the analog signal is done with 512×the desired target scan rate of 160 Hz; that is, using 81.92 kHz. Each channel has an analog and "soft" wired Butterworth filter for this purpose that effects practically no signal influence. After the A/D conversion the required band limitation for the target scan rate as well as the reduction of the scan rate by a factor of 512 is executed via sharp, linear-phase digital filters.

In particular, the filters used have the following properties:

A filter pass band/range (−3 dB) at 48% of the target scan rate

End of the filter pass band (−0.01 dB) at 44% of the target scan rate

Beginning of the stop band (−80 dB) at 56% of the target scan rate.

An external reference voltage source for all four converters results in a high level-precision with fluctuation of less than 0.1%. Two digital signal processor cards and one V40 microprocessor, as well as memory in the form of 1 MB RAM on the card relieve the PC and take over the communications with the digital signal processor card.

The digital signal processor card uses the 32-bit floating-point processor ADSP 21020, which outputs up to 60 MFLOPS. In this way, it can calculate, for example, a fast Fourier transformation of 1024 points on four channels up to a data rate of 20 kHz in real time. The massive surplus in computing performance relevant to the requirements is used to relieve the PC to work with overlapping data windows, to make reports, and to prepare graphics. The 32-bit spectrum of the processors assures the high signal-to-noise spacing, which is greater than 140 dB in the fast Fourier transformation (=FFT) in the present example, already processed by the measured value acquisition card. The data present at the output end of the digital signal processor card have a 16 bit spectrum and whole number values in the range of ±32767. The target data rate of 160 Hz is selected in such a manner that the maximum measurable frequency in the performance of the FFT is 80 Hz and thus, there is an additional interval with the factor of 4 is present in the frequency considered in the evaluation.

What follows next is storage of the signals on the hard disk (4) of the PC, which is equipped with the cards. A prototype consisting of a notebook with a docking station has proved to be practical because of its easy handling characteristics at the patient's bedside. It can remain on the bed or on a frame that is mounted on the bed. In this case, there is no unnecessary cabling to a stationary computer stack that would make patient care more difficult. In addition the apparatus described in this realization example can also be adapted to an existing system for monitoring of a patient in a so-called stroke unit (stroke intensive care unit), with which additional electrocardiogram, blood pressure, $O_2$ saturations, etc. can be done. In the present example, the recorder program manufactured by STAC GmbH was used for signal storage; it is optimally adapted to cards made by that company. It permits online storage of the two differentially amplified EEG channels (respectively central/-temporal against mastoid) on a conventional commercial hard disk. In this case files of the order of 10 min=160 Hz * 2 channels * 2 byte 384,000 bytes per derivation are created. During acquisition, the signal itself as well as, for example, its range can be displayed on the notebook monitor (5) screen.

Following a completed signal measurement the actual analysis (8), (9), (10), (11) of the signals from the saved file takes place. This means that there is, on the one hand, no disadvantage vis-à-vis a direct online analysis, because the measurement time of 5–10 minutes is sufficiently brief and the following analysis can be performed in approximately the half of the real time and, on the other hand, there is the advantage that the analysis can be repeated at any time, for example, using changed parameters. On a system with sufficient performance capability, it is conceivable that the analysis can be done parallel with signal storage.

Analysis of a discrete, but not time-limited signal by a discrete Fourier transformation (=DFT) always required parceling into blocks. When doing this, attention must be paid that the frequency resolution; that is, the lowest measurable frequency, and the maximum measurable frequency are set by the block length and the scanning rate. The following relationships apply between these:

Frequency Resolution $\Delta f = f_s/N$ Time Signal–Block Length $T = N*\Delta t = N/f_s$ Time Resolution $\Delta t = 1/f_S$ Scan Rate $= f_S = 1/\Delta t$ It is particularly important that the signal prior to digitizing does not contain frequency content above the half sampling or scanning rate, that could become noticeable by aliening effects and could strongly distort the effects (scan theorem). The adaptation of the anti-aliening filter is already done on the hardware side by the measured value acquisition card with the scanning rate set on the software side (STAC recorder).

The correlation function of two grid integratable functions f1 and f2 is mathematically defined as:

$$C(\tau) = \int f_1(t) f_2(t+\tau) dt = \sum_{t=1}^{N} f_1(t) f_2(t+\tau)$$

It cannot, therefore, be calculated for temporally unrestricted signals that are generally not grid-integratable. If the f1 and f2 signals are broken down into overlapping blocks ("data windows"), the correlation of two functions, that are produced within the data window by the signal and externally are equal to zero, can be calculated. The "functions" present here are naturally not continuous, but discretely defined by scanning or sampling so that in summation in place of the integral. This calculation of the cross-correlation then provides a discrete function that defines an interval of double the length T of the original signal and external to the interval (−T, T) is equal to zero.

In such correlation, functions in similar applications are calculated by means of an inverse Fourier transformation from FFT of the individual signals; this has advantages from the aspect of numeric overhead. Nevertheless, the DFT continues the time-signal continues precisely periodically after a block length which then generally results in an irregular signal track. In order to avoid discontinuity effects, the signal is normally multiplied prior to transformation using a data function like, for example, the Hanning window, which differentiably reduces the signal at the margins of the block to zero, and functions using an overlap of the data window by more than 60%. This is, however, not appropriate in the calculation of the cross-correlation function (=CCF), since a data function would have too great an affect on the signal and would enter too powerfully into the CCF. The requirement of scanning the signal with a large "overlap" or using large overlapping is eliminated for this reason, since no attenuated signal information at the edge of two blocks. Pursuant to this example, the cross-correlation is therefore calculated directly in accordance with the summation formula given above.

The calculated correlation (8) describes the extent to which the signal of one channel approximates the signal of another channel when it is shifted by a certain time. Consequently, it can detect coherence between the two brain hemispheres. Now, in order to find out whether the same basic frequency is synchronously present in both brain hemispheres the correlation function itself undergoes a fast Fourier transformation or FFT (9). When this is done the scanning rate is halved; that is, the frequency resolution is doubled. The range of 0–20 Hz is displayed from the spectrum of the cross-correlation function or CCF that then includes 128 points. This point of view applies to the availability of one or several peak values or "peaks" in the CCF spectrum in the range of from 3 to 14 Hz, preferably from 7 to 12 Hz. Since this peak must not be permanently present even in the healthy human being, a temporal average value over a period of time of from one to ten minutes is created in the form of a histogram.

The block length of 512 values has been obtained from the test series done using the foregoing realization example. With a sampling rate of 160 Hz this corresponds to a data window size of (T=$512/160$ Hz=) 3.2 seconds and a frequency resolution of ($\Delta f=1/3.2$ sec.=) 0.3 Hz. Thus 64 points are eliminated at the frequency range of 0–20 Hz that is of interest for subsequent analysis. For the purposes of testing, 60% overlap was used; this corresponds to "new" values in 1.28 seconds per block with 3.2 seconds. In practice, a modest overlap of approximately 10% is recommended.

When forming a diagnosis the hypothesis is made that the extent of the brain insult caused by the circulatory perturbation is based on how competent the two brain hemispheres are to still produce α-frequencies, to "synchronize" themselves, and to function "in phase." In healthy persons, said "synchronization" and "in-phase" function is produced in the frequency range of from 3 to 14 Hz and preferably in the range of 7 to 12 Hz; the so-called α-range or the "basic rhythm." First, in order to achieve this it is necessary that such frequency content is measured in both brain hemispheres; that is, it must be measured on both channels. Second, it is necessary that this frequency content be in both hemispheres at the same frequency. Therefore, pursuant to the invention, not only the spectra of the individual signals (11) are examined but a function is also considered that measures the "similarities" of the two channels in the form of the cross-correlation function (8). Only when the basic rhythm on both sides is at the same frequency will the corresponding frequency components appear also in the cross-correlation. A so-called brain function index ("HFI") (6) is calculated in a dimension for the normalcy of the brain function of the person being examined. It can assume the four words "Normal," "Mildly Affected," and "Pathology." Its determination cannot, however, be supported solely by the signal analysis. For example, it is well-established that young persons under the age of 20 years do not yet show definite α-rhythms and that the EEG of persons who are under the influence of medications (tranquilizers, analgesics, valium) can be very substantially altered.

Therefore, clinical parameters (7) are included in the calculation of the brain function index. Such parameters (7) are, for example, age of the patient or the influence of medications. The brain function index is thus calculated from:

Age and the influence of medications;

Signal quality of the parameters determined using the apparatus for measurement of brain currents;

Frequency peak between 3 and 14 Hz, preferably between 7 and 12 Hz on both channels of the FFT of the EEG signal;

Frequency peak between 3 and 14 Hz, preferably between 7 and 12 Hz in the FFT of the cross-correlation function;

Sharp distribution in the histogram of the frequencies of the peaks in the FFT of the cross-correlation, and The number of simultaneously occurring frequency peaks in the α-range.

The following allocations are done in the case with good signal quality in a patient over 20 years of age, who is not under the influence of tranquilizing agents:

If the FFT of an EEG on one side does not show a peak in the range stated above and the correlation functions and the histogram also show no such peak, then the HFI=Pathology.

If the FFT of an EEG on both sides show a peak in the range stated above and the correlation function and the histogram also show such a peak, then the HFI=Normal.

If the FFT of an EEG on one side happens to show a peak in the range stated above and the correlation function happens not to show a peak in the range stated above and the histogram (as average) shows such a peak (even if of weaker definition), then the HFI=Mildly Affected.

This invention offers the user the opportunity to obtain important and meaningful supplemental information regarding the diagnosis in a patient presenting with stroke in the acute phase. The evaluation is rapidly made along the lines of stored data measurements and, because the data are stored, the assessment can be repeated as often as desired. For the purposes of assessment, both the measured brain signals and the evaluation of these measured values is done with the assistance of supplemental information on the patient and entered as parameters. A short report on the severity of the damage in the form of a so-called brain function index is output as the result of the assessment by the device described in the invention using the process according to the invention.

What is claimed is:

1. An apparatus for measuring and analyzing the brain currents of both brain hemispheres of a patient comprising:
    a means (1) for measuring brain currents in the two brain hemispheres of a patient in the form of electrical signals by application of several measurement electrodes on the patient's head;
    an amplifier (2) for amplifying the measured signals;
    a computer with accessories, including an A/D converter (3) for conversion of amplified analog signals into digital signals;
    a means (8) for calculation of the cross-correlation function (CCF) from the digitized signals of the two individual channels in order to ascertain the extent to which the measured signals from two channels are similar from a measurement of the coherence of the electrical activity between the two brain hemispheres of a patient, from which the cross-correlation function (CCF) is obtained;
    a memory (4) for storage of the digitized signals;
    a means (11) for application of a fast Fourier transformation in a given frequency range to the digitized signals and/or the stored digitized signals of the two individual channels for the purpose of calculating and comparing the structure of the spectra of the individual signals;
    a means (9) for applying a fast Fourier transformation (FFT) to the cross-correlation function in a certain frequency range in order to calculate and analyze the spectra of the cross-correlation function, the purpose of which is to ascertain whether in both brain hemispheres the same basic frequencies are synchronously present, and;
    a means (6) for determining the brain function index as the measurement for the normalcy of the patient's brain function, which is determined by the use of both a cross-correlation function which has been subjected to a fast Fourier transformation (FFT) and the signals of both individual channels subjected to a fast Fourier transformation (FFT).

2. The apparatus of claim 1 wherein the means (8) separates the digitized signals, prior to calculation of the cross-correlation function (CCF) in a data range, into overlapping blocks for the purpose of calculating the cross-correlation function (CCF) of the two individual channels.

3. The apparatus of claim 1 wherein the means (11) blocks, prior to the application of the fast Fourier transformation (FFT), and separates the signals into overlapping blocks for the purpose of application of a fast Fourier transformation (FFT) on the digitized and/or the stored digitized signals of the two individual channels.

4. The apparatus of claim 1 further comprising:
    supplement utilities of the computer which further include a means (10) for the creation of a histogram of frequency peaks from which the cross-correlation functions subjected to the fast Fourier transformation (FFT) are shown in a particular frequency range for the purpose of determining an amplitude distribution in said range, and whereby by analysis of the structure of the entire signal that is composed of the signals of both channels and the cross-correlation function (CCF), characteristic numbers are calculated for current blocks in the frequency range, which are then temporally averaged over a given time period and from whose averaging the brain function index is calculated.

5. The apparatus of claim 1 further comprising:
    additional display means (5, 6) for displaying measures signals and/or the derived brain function index, whereby the digitized signals can be displayed on the display means during signal pickup.

6. The apparatus of claim 5 wherein the display means (5, 6) display the determined brain function index in text and/or graphics as the diagnostic result in the form of, for example, "HFI=Pathology," "HFI=Normal," or "HFI=Mildly Affected" or as an index or numeric value that is concise and generally understandable.

7. The apparatus of claim 1 further comprising:
    an input means (7) which is used for entering useful additional parameters into a means (6) at the time of determining the brain function index and for the purpose of determining the brain function index and which, for example, may be the age of the patient and or information relating to medications being taken.

8. The apparatus of claim 1 further comprising:
    a call-up means (7) which is used, at the time of determining the brain function index, for the purpose of calling up previously stored useful additional parameters that can be, for example, the age of the patient and/or information relating to medications being taken.

9. The apparatus in claim 1 which can be integrated into an existing system for the purpose of measuring other values for the purpose of diagnosis.

* * * * *